United States Patent
Hood et al.

(10) Patent No.: US 9,164,065 B2
(45) Date of Patent: Oct. 20, 2015

(54) AUTOMATED FAULT LOCALIZATION IN PIPELINES AND ELECTRICAL POWER TRANSMISSION LINES

(71) Applicant: Telefonaktiebolaget L M Ericsson (publ), Stockholm (SE)

(72) Inventors: David Hood, Palo Alto, CA (US); Stefan Dahlfort, Santa Clara, CA (US)

(73) Assignee: TELEFONAKTIEBOLAGET L M ERICSSON (PUBL), Stockholm (SE)

( * ) Notice: Subject to any disclaimer, the term of this patent is extended or adjusted under 35 U.S.C. 154(b) by 561 days.

(21) Appl. No.: 13/797,589

(22) Filed: Mar. 12, 2013

(65) Prior Publication Data
US 2014/0260638 A1    Sep. 18, 2014

(51) Int. Cl.
G01R 31/02    (2006.01)
G01N 29/14    (2006.01)

(52) U.S. Cl.
CPC ....................................... *G01N 29/14* (2013.01)

(58) Field of Classification Search
CPC .. G01R 31/088; G01R 31/083; G01R 31/085; G01R 31/3275
USPC ......................................... 324/532, 527–531
See application file for complete search history.

(56) References Cited

U.S. PATENT DOCUMENTS

| | | | |
|---|---|---|---|
| 5,508,619 A * | 4/1996 | Ozawa et al. ................. | 324/535 |
| 6,715,354 B2 | 4/2004 | Wooh | |
| 6,854,333 B2 | 2/2005 | Wooh | |
| 2004/0189317 A1* | 9/2004 | Borchert et al. .............. | 324/512 |
| 2008/0232795 A1 | 9/2008 | Klar et al. | |
| 2012/0224846 A1 | 9/2012 | Swanson et al. | |

FOREIGN PATENT DOCUMENTS

EP    1001271 B1    1/2007

OTHER PUBLICATIONS

Bhatia, M., et al., "IS-IS Generic Cryptographic Authentication", RFC 5310; Feb. 2009; 12 pages.
Callon, R., et al., "Use of OSI IS-IS for routing in TCP/IP and Dual Environments", RFC 1195; Dec. 1990; http://tools.ietf.org/rfc/rfc1195.txt; 80 pages.
Chunduri, U., et al., "KARP IS-IS Security Gap Analysis draft-chunduri-karp-is-is-gap-analysis-03", Oct. 12, 2012; 13 pages.

(Continued)

*Primary Examiner* — Vincent Q Nguyen
(74) *Attorney, Agent, or Firm* — Nicholson De Vos Webster & Elliott LLP

(57) ABSTRACT

Methods and apparatus for determining an estimated physical location of a fault in a pipeline or electrical transmission line using localization devices coupled thereto. In an embodiment, a first and second localization device each generate time values representing times when the respective localization device detected the fault. The estimated fault location is calculated, by one of the localization devices or a separate computing device, based upon the reported time values. In some embodiments, the calculation is further based upon characteristics of the pipeline or electrical transmission line, or based upon characteristics of matter transported through the pipeline. In some embodiments, the localization devices transmit time or sequence values to the other device, and the values received by the devices just before the detection of the fault may additionally be utilized to calculate the estimated physical location of the fault.

24 Claims, 10 Drawing Sheets

(56) References Cited

OTHER PUBLICATIONS

Hartman, S., et al., "Multicast router Key Management Protocol draft-hartman-karp-mrkmp-05", Sep. 6, 2012; 27 pages.

Li, T., et al., "IS-IS Cryptographic Authentication", RFC 5304; Oct. 2008; 12 pages.

Tran, P., et al., "The Use of G-IKEv2 for Multicast Router Key Management draft-tran-karp-mrmp-02", Oct. 22, 2012; 13 pages.

"Speed of Sound," Nov. 3, 2012, 17 pages, Wikipedia, downloaded from http://web.archive.org/web/20121103193755/http://en.wikipedia.org/wiki/Speed of sound on Jun. 9, 2014.

D. Mills et al., "Network Time Protocol Version 4: Protocol and Algorithms Specification," Jun. 2010, 110 pages, Internet Engineering Task Force (IETF), Request for Comments: 5905, IETF Trust and the persons identified as the document authors.

IEEE Standard for a Precision Clock Synchronization Protocol for Networked Measurement and Control Systems, *IEEE Std 1588-2008* (Revision of IEEE Std 1588-2002), 2008, 1-269.

"Part 11: Wireless LAN Medium Access Control (MAC) and Physical Layer (PHY) Specifications," IEEE 802.11-2012; *IEEE Standard for Information technology; Telecommunications and information exchange between systems; Local and metropolitan area networks; Specific requirements*, Mar. 29, 2012, 2793 pages.

Non-Final Office Action, U.S. Appl. No. 13/677,264, dated Sep. 15, 2014, 14 pages.

Notice of Allowance, U.S. Appl. No. 13/677,264, dated Dec. 1, 2014, 6 pages.

Notice of Allowance, U.S. Appl. No. 13/677,263, dated Dec. 5, 2014, 17 pages.

"Network Time Protocol", 6 pages, Wikipedia, downloaded from http://en.wikipedia.org/wiki/Network_Time_Protocol on Mar. 12, 2013.

Notice of Allowance for U.S. Appl. No. 13/677,264, mailed Jul. 7, 2015, 6 pages.

\* cited by examiner

```
RECEIVING, FROM A FIRST LOCALIZATION DEVICE COUPLED TO THE PIPELINE AT A
FIRST LOCATION, A FIRST OBSERVED TIME VALUE INDICATING A TIME WHEN THE
FIRST LOCALIZATION DEVICE DETECTED A DISTURBANCE CAUSED BY THE FAULT,
WHEREIN THE DISTURBANCE COMPRISES ONE OR MORE OF (1) AN ARRIVAL OF AN
ACOUSTIC WAVE AT THE FIRST LOCATION, AND (2) A CHANGE, AT THE FIRST
LOCATION, IN A FLOW RATE OR PRESSURE OF MATERIAL TRANSMITTED THROUGH
THE PIPELINE
705
```

```
RECEIVING, FROM THE FIRST LOCALIZATION DEVICE, A FIRST TIMING VALUE THAT IS
A LAST TIMING VALUE OF A FIRST PLURALITY OF TIMING VALUES RECEIVED BY THE
FIRST LOCALIZATION DEVICE FROM THE SECOND LOCALIZATION DEVICE PRIOR TO
SAID TIME THAT THE FIRST LOCALIZATION DEVICE DETECTED THE DISTURBANCE 710
```

```
RECEIVING, FROM A SECOND LOCALIZATION DEVICE COUPLED TO THE PIPELINE AT
A SECOND LOCATION, A SECOND OBSERVED TIME VALUE INDICATING A TIME WHEN
THE SECOND LOCALIZATION DEVICE DETECTED THE FAULT 715
```

```
RECEIVING, FROM THE SECOND LOCALIZATION DEVICE, A SECOND TIMING VALUE
THAT IS A LAST TIMING VALUE OF A SECOND PLURALITY OF TIMING VALUES
RECEIVED BY THE SECOND LOCALIZATION DEVICE FROM THE FIRST LOCALIZATION
DEVICE PRIOR TO SAID TIME THAT THE SECOND LOCALIZATION DEVICE DETECTED
THE FAULT 720
```

```
CALCULATING THE ESTIMATED PHYSICAL LOCATION OF THE FAULT BASED UPON
THE FIRST OBSERVED TIME VALUE AND THE SECOND OBSERVED TIME VALUE
[AND FURTHER BASED UPON THE FIRST TIMING VALUE AND THE SECOND TIMING
VALUE] 725
```

AUTOMATED FAULT LOCALIZATION IN PIPELINES AND ELECTRICAL POWER TRANSMISSION LINES

FIELD

Embodiments of the invention relate to the field of fault localization; and more specifically, to the determination of an estimated physical location of faults in pipelines and electrical power transmission lines.

BACKGROUND

Whether they carry gas, liquids or electrical energy, utility lines that span geographic regions can fail for a number of reasons, including seismic events, windstorms, falling debris, and byproducts of human actions. Such failures are particularly important because they can be catastrophic to life, such as in the case of a complete failure of a pipeline carrying explosive or toxic matter. Additionally, these failures are expensive in terms of both the labor and time required to locate the failure and repair the line, in addition to the cost and negative publicity of the resulting loss of service occurring during this time. Accordingly, it is of the utmost of importance to be able to efficiently monitor and troubleshoot utility lines to ensure safety and availability of service.

Fault detection apparatus is already present in some types of existing utility lines. For example, breakers in electrical transmission lines may be coupled to telemetry systems that indicate breaker trippage to remote operation centers of utility companies. However, the fact that a breaker has tripped only isolates the fault to the segment downstream of the tripped breaker or between a pair of tripped breakers. Due to the length, remote geographic placement, and/or difficulty of access to many utility lines, substantial time and cost could be saved if a more precise location of a fault were readily available, preferably through automated means.

SUMMARY

Methods for determining an estimated physical location of a fault in utility lines are described. According to an embodiment of the invention, a method in a localization device coupled to a pipeline at a first location is described for determining an estimated physical location of a fault in the pipeline. The method includes detecting, by the localization device, a disturbance caused by the fault. The disturbance comprises one or more of an arrival of an acoustic wave at the first location, and a change, at the first location, in a flow rate or pressure of matter transmitted through the pipeline. The method further includes determining a first observed time value indicating a time when the localization device performed said detecting of the disturbance, and receiving, from a second localization device coupled to the pipeline at a second location, a second observed time value indicating a time when the second localization device detected the fault. Then, the localization device calculates the estimated physical location of the fault based upon the first observed time value and the second observed time value. In some embodiments, this calculation is also based upon one or more of a propagation velocity of the matter transmitted through the pipeline, a propagation velocity of acoustic waves in the matter transmitted through the pipeline or transmitted through its walls, a length of the pipeline between the first and second sensor locations, and an acoustic wave propagation delay of the pipeline between the first and second sensor locations. In an embodiment, the method further includes receiving a first plurality of timing values transmitted by the second localization device, and transmitting a second plurality of timing values to the second localization device. The method further includes determining that a first timing value of the first plurality of timing values is a last timing value of the first plurality of timing values received by the localization device prior to said detecting of the disturbance, and receiving a second timing value from the second localization device that is a last timing value of the second plurality of timing values received by the second localization device prior to said time when the second localization device detected the fault. In an embodiment, the calculating of the estimated physical location of the fault is further based upon the first timing value and the second timing value.

In an embodiment of the invention, a method for determining an estimated physical location of a fault in a pipeline is performed in a computing device. The method includes receiving, from a first localization device coupled to the pipeline at a first location, a first observed time value. The first observed time value indicates a time when the first localization device detected a disturbance caused by the fault. The disturbance comprises one or more of an arrival of an acoustic wave at the first location, and a change, at the first location, in a flow rate or pressure of matter transmitted through the pipeline. The method also includes receiving, from a second localization device coupled to the pipeline at a second location, a second observed time value. The second observed time value indicates a time when the second localization device detected the fault. The method further includes calculating the estimated physical location of the fault based upon the first observed time value and the second observed time value. In an embodiment, the calculation is further based upon one or more of a propagation velocity of the matter transmitted through the pipeline, a propagation velocity of acoustic waves transmitted through the matter transmitted through the pipeline or transmitted through the walls of the pipeline, a length of the pipeline between the first and second locations, and an acoustic wave propagation delay of the pipeline between the first and second locations. In an embodiment, the method also includes (1) receiving, from the first localization device, a first timing value that is a last timing value of a first plurality of timing values received by the first localization device from the second localization device prior to said time that the first localization device detected the disturbance, and (2) receiving, from the second localization device, a second timing value that is a last timing value of a second plurality of timing values received by the second localization device from the first localization device prior to said time that the second localization device detected the fault. In an embodiment, the calculating of the estimated physical location of the fault is further based upon the first timing value and the second timing value.

According to an embodiment of the invention, a method in a localization device coupled to an electrical power transmission line at a first location is described for determining an estimated physical location of a fault in the electrical power transmission line. The method includes detecting, by a localization device, a disturbance caused by the fault, wherein the disturbance is propagated through the electrical power transmission line. The method also includes determining a first observed time value indicating a time when the localization device detected the disturbance. The method further includes receiving, from a second localization device coupled to the electrical power transmission line at a second location, a second observed time value indicating a time when the second localization device detected the fault, and then calculating the estimated physical location of the fault based upon the first observed time value and the second observed time value. In an embodiment, the calculation is further based upon one or more of a propagation velocity of the electromagnetic energy transmitted over the electrical power transmission line and a length of the electrical power transmission line between the first and second locations.

In another embodiment of the invention, a method performed in a computing device is described for determining an estimated physical location of a fault in an electrical power transmission line. The method includes receiving, from a first localization device coupled to the electrical power transmission line at a first location, a first observed time value indicating a time when the first localization device detected a disturbance, caused by the fault, which propagated through the electrical power transmission line. The method also includes receiving, from a second localization device coupled to the electrical power transmission line at a second location, a second observed time value indicating a time when the second localization device detected the fault. The method further includes calculating the estimated physical location of the fault based upon the first observed time value and the second observed time value. In an embodiment, the calculation is further based upon one or more of a propagation velocity of the electromagnetic energy transmitted over the electrical power transmission line and a length of the electrical power transmission line between the first and second locations.

Accordingly, disclosed embodiments of the invention allow for rapid and accurate localization of faults in pipelines and electrical power transmission lines without the need for significant additional hardware or physical labor.

BRIEF DESCRIPTION OF THE DRAWINGS

The invention may best be understood by referring to the following description and accompanying drawings that are used to illustrate embodiments of the invention. In the drawings:

FIG. 7 illustrates a flow for determining an estimated physical location of a fault in a pipeline by a computing device according to an embodiment of the invention;

DESCRIPTION OF EMBODIMENTS

Figure 1:
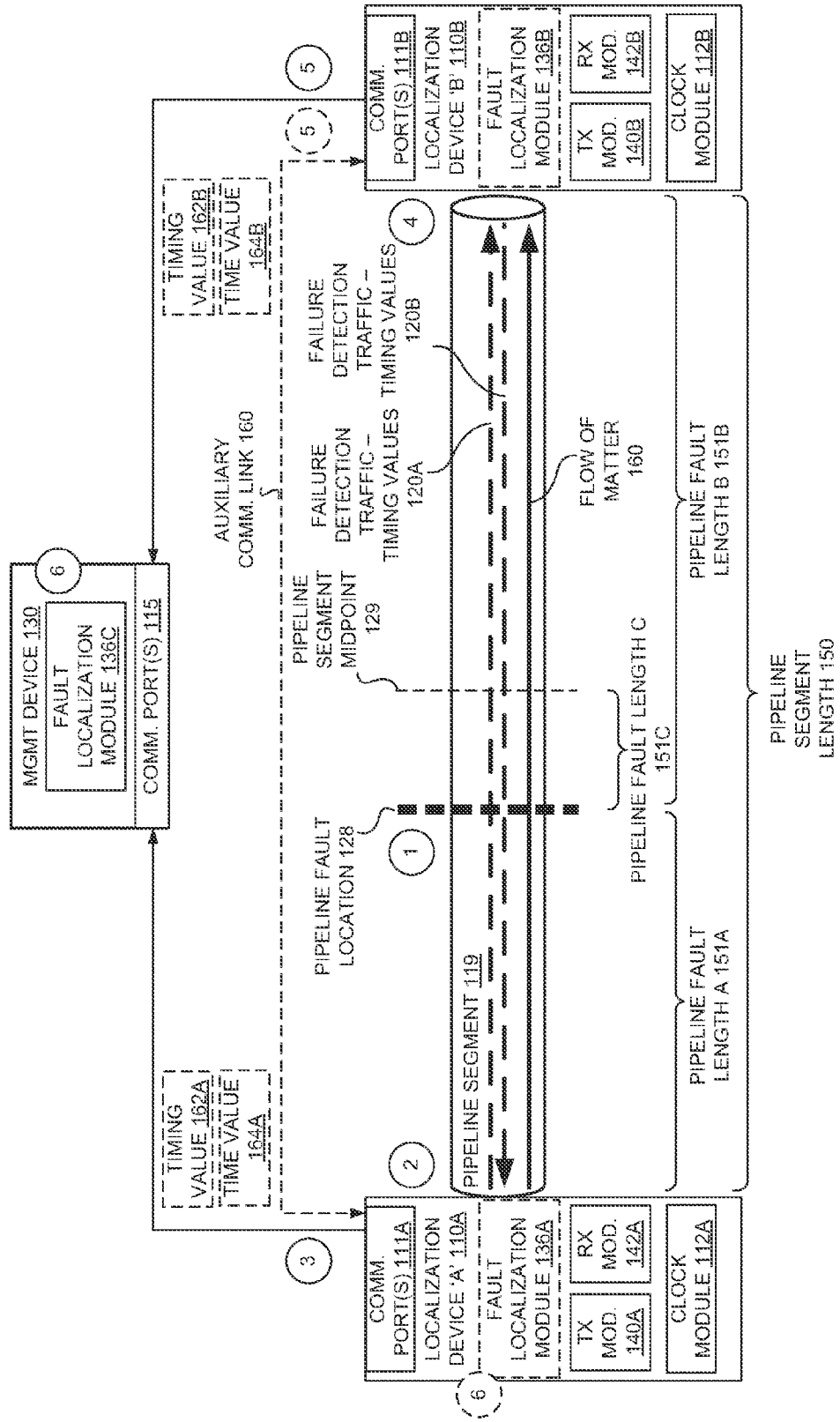
FIG. 1 illustrates a system configuration for localizing faults in a pipeline according to an embodiment of the invention.

In the following description, numerous specific details are set forth. However, it is understood that embodiments of the invention may be practiced without these specific details. In other instances, well-known circuits, structures and techniques have not been shown in detail in order not to obscure the understanding of this description. Those of ordinary skill in the art, with the included descriptions, will be able to implement appropriate functionality without undue experimentation.

References in the specification to "one embodiment," "an embodiment," "an example embodiment," etc., indicate that the embodiment described may include a particular feature, structure, or characteristic, but not every embodiment may necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to implement such feature, structure, or characteristic in connection with other embodiments whether or not explicitly described.

In the following description and claims, the terms "coupled" and "connected," along with their derivatives, may be used. It should be understood that these terms are not intended as synonyms for each other. "Coupled" is used to indicate that two or more elements, which may or may not be in direct physical or electrical contact with each other, cooperate or interact with each other. "Connected" is used to indicate the establishment of communication between two or more elements that are coupled with each other.

In some embodiments of the invention, an electronic device is utilized to perform fault localization. An electronic device (e.g., a computing device, an end station, a network element) stores and transmits (internally and/or with other electronic devices over a network) code (composed of software instructions) and data using computer-readable media, such as non-transitory tangible computer-readable media (e.g., computer-readable storage media such as magnetic disks; optical disks; read only memory; flash memory devices) and transitory computer-readable transmission media (e.g., electrical, optical, acoustical or other form of propagated signals—such as carrier waves, infrared signals). In addition, such electronic devices typically include a set of one or more processors coupled to one or more other components, such as one or more non-transitory machine-readable media (to store code and/or data), user input/output devices (e.g., a keyboard, a touchscreen, and/or a display), and network connections (to transmit code and/or data using propagating signals). The coupling of the set of processors and other components is typically through one or more busses and bridges (also termed as bus controllers). Thus, a non-transitory computer-readable medium of a given electronic device typically stores instructions for execution on one or more processors of that electronic device. One or more parts of an embodiment of the invention may be implemented using different combinations of software, firmware, and/or hardware.

In this description, the term "localization device" indicates a potentially complex device or group of devices working in concert, and including "sensing" apparatus and possibly transducer apparatus. A localization device may be an electronic device or contain electronic devices. With respect to localization devices utilized with pipelines, such devices may be capable of detecting or measuring pressure waves in a fluid medium, and possibly also flow rate in a fluid medium or acoustic waves in the walls of the pipeline material itself. A localization device, in certain embodiments, is capable of recognizing anomalies in an acoustic wave or flow rate and generating time stamps designating the time at which the anomaly is recognized. In some embodiments, a localization device is capable of some or all of generating and detecting communications signals, recognizing time stamps or decoding encoded time stamp information transmitted from a remote localization device, analyzing fault information to determine an estimated physical location of a fault, and communicating fault detection or analysis information to an external processing or monitoring system.

Aspects of the invention are applicable to be used for the automatic determination of estimated fault locations in pipelines. Pipeline transport, which is the transportation of matter (including but not limited to liquids and gases, such as but not limited to oil and refined oils including gasoline and kerosene, natural gas, biofuels including ethanol and biobutanol, water, oxygen, air, hydrogen, ammonia, etc.) through a pipe, is vulnerable to disruptions by failures in the pipeline. For example, portions of pipelines may be affected by leaks or breakage due to corrosion of the pipeline, environmental factors such as seismic events, windstorms, and falling debris, and/or inadvertent or intentional damage caused by a person, machine, or animal. Further, because many pipelines are very long or not easy to access (e.g., buried underground, placed in remote locations, placed underwater, etc.), it can be challenging to quickly identify a pipeline fault location. At the same time, it is often critically important to identify pipeline faults to prevent damage to the environment, loss of the matter being transmitted through the pipeline, and disruptions of service to customers that rely upon the pipeline.

In a pipeline or aqueduct subject to sudden rupture, a sonic pressure wave may be expected to propagate both upstream and downstream from the fault location toward sensors (deemed herein as "localization devices") equipped to monitor the pipeline, where the sonic wave may be observed with a pressure detector or other sensing apparatus sensitive to the properties of the pipeline and/or transported matter. In addition, the flow rate may change suddenly, increasing at the upstream localization device and decreasing at the downstream localization device, and the change in flow rate also propagates at the speed of sound in the matter of the pipeline. Using embodiments of the invention, it is also possible to detect and localize partial failures, for example a leak developing in the pipeline. Embodiments of the invention may also detect the opening or closing of a valve along the pipeline segment, as these events similarly create a detectable change in the transported matter and/or pipeline itself, and the detection of such changes may be a way to monitor the integrity of the localization devices and their associated analysis and reporting component modules. It may be desirable to arrange alarm declaration algorithms to correlate such known and intentional operations of the pipeline with event analyses performed by the methods and systems taught herein.

Certain embodiments of the invention for pipeline fault location determination utilize time measurements, such as the times of fault detection at the two localization device locations. Certain embodiments also use time (or sequence) information from data transmitted in each direction through the pipeline itself between localization devices. Such embodiments work well for pipelines for reasons including, for example, the variable speed of sound in fluid, daily and/or seasonal temperature changes, and possibly variation in fluid composition in the pipeline flow (e.g., different grades of petroleum products). In these embodiments, a signal is injected into the matter within the pipeline at each detection point, which carries timing information. In an embodiment, for example, the localization devices include an acoustic transducer for injecting this information.

In an embodiment, the injected information (or, "failure detection traffic") includes digital timestamp or sequence values (time aliases) transmitted by each detection point, wherein each value is encoded acoustically. An embodiment for pipelines utilizes a Pseudo-random Binary Sequence (PRBS) as a proxy for a time stamp, the PRBS generated by a linear feedback shift register or its equivalent, with each '1' bit indicated by a tone at a first frequency and each '0' bit indicated by a tone at a second frequency that differs from the first frequency. In some embodiments, nothing is transmitted to represent one of the bit values, for example the '0' bit, although this may reduce the system's localization resolution in detecting failure events. Some embodiments may utilize composite tones at two or more frequencies to represent the injected data. It is understood that, in any of these embodiments, Doppler shift compensation may be used for aligning tone frequencies through the matter moving through the pipeline.

The speed of sound in fluid is on the order of a million times slower than the speed of light. Accordingly, as compared to the use of the same principles in electromagnetic media, comparable geographic resolution can be achieved with technology that achieves approximately a million times less precision, for example in detecting the start time of a fault signature pressure wave. It is also possible to use the difference in propagation velocity to greatly relax the requirements for precise time of day synchronization between sensor locations. For example, it may be easy to achieve 10 millisecond agreement between clock sources using uncompensated radio or landline communications techniques; an error of 10 ms in timing accuracy implies an error of 10 feet in an acoustic environment with 1000 feet/second propagation velocity.

FIG. 1 illustrates a system configuration for localizing faults in a pipeline segment according to an embodiment of the invention. The system includes a pipeline segment 119 coupled to a localization device 'A' 110A at a first location and a localization device 'B' 110B at a second location. Each localization device 110A-110B may, in some embodiments, be an electronic device as defined above. In an embodiment, each localization device 110A-110B may be located at a Pipeline Inspection Gauge (PIG) Launch/Recovery Facility, pump station, compressor station, point of origination or termination, or any other point of the pipeline. The pipeline carriers a flow of matter 160, which in the depicted embodiment flows in the direction from localization device 'A' 110A toward localization device 'B' 110B.

In the depicted embodiment, at circle '1' a failure in the pipeline occurs at a pipeline fault location 128. Depending upon the type of pipeline segment 119 and the type of matter being transported through the pipeline segment 119, evidence of the fault will be detected by each of the localization devices 110A-110B after a period of time. In an embodiment, each localization device 110A-110B is operable to detect the fault by detecting a "fault signature" associated with the fault. A fault signature is a detectable occurrence or evidence associated with a pipeline fault, which may be detected in the matter being transported through the pipeline, detected within the pipeline segment 119 material (e.g., walls) itself, or detected in the surrounding environment external to the pipeline segment 119 that indicates that the fault occurred. For example, in an embodiment, a fault signature is a sudden drop in pressure within the pipeline segment 119, as a sudden rupture of the pipeline segment 119 will cause a sonic pressure wave to propagate toward each localization device 110A-110B. In certain embodiments, a fault signature is a change in the flow rate of the matter 160 in the pipeline segment 119: the localization device 'A' 110A, which is located above the failure, may detect a sudden increase in flow rate, and localization device 'B' 110B, which is located below the failure, may detect a decrease in flow rate. In an embodiment, upon detection of the fault signature, each localization device 110A-110B will utilize a clock module 112A-112B to determine a time when the fault signature was detected.

It is important to note that for pipelines, due to the flow of matter 160 and the properties of the matter, a pipeline fault occurring geometrically closer (i.e., geographically closer) to one of the localization devices 110A-110B may not be first detected by that closer device. This occurs because the effective speed of sound in the downstream direction of a flow of matter is greater than the effective speed of sound upstream, the difference being the flow rate of the matter itself.

In the depicted embodiment of FIG. 1, however, at circle '2' localization device 'A' 110A determines that the fault occurred via detecting a fault signature from the pipeline segment 119, determines a time value of the detection of the fault, and at circle '3' transmits the time value 164A using a set of one or more communication ports 111A (e.g. network interfaces) to the management device 130. At circle '4', the evidence of the fault arrives at and is detected by localization device 'B' 110B (i.e., localization device 'B' 110B detects a fault signature), which similarly may determine a time value of its detection of the fault. At circle '5', the localization device 'B' 110B transmits the time value 164B using a set of communication ports 111B to the management device 130. At circle '6', using the two reported time values (received at a set of one or more communication ports 115) and known properties of the pipeline segment 119 and/or matter transported through the pipeline segment 119 (including but not limited to the length 150 of the pipeline segment, a propagation velocity or propagation delay of the matter being transmitted through the pipeline, and/or the velocity of propagation or propagation delay of acoustic waves in the matter transported in the pipeline), the management device 130 calculates one or more of a distance from localization device 'A' 110A to the fault location 128 (i.e., pipeline fault length 'A' 151A), a length from the midpoint 129 between sensors 110A and 110B to the fault location 128 (i.e., pipeline fault length 'C' 151C), a distance from localization device 'B' 110B to the fault location 128 (i.e., pipeline fault length 'B' 151B), or a geographic location (e.g., latitude and/or longitude location, nearest street or intersection location, plot location, city location, etc.) based upon one or more of those distances. In an embodiment, there are more than two localization devices that report time values to a management device 130 when each respective localization device detects the fault signature, and the fault localization module 136C will base its calculation of the physical location of the pipeline fault 128 upon the more than two reported time values. Additional details regarding the computation of the fault location, according to one embodiment of the invention, are presented in FIG. 2 and its associated textual description.

The system of FIG. 1, in some embodiments, may not include a separate management device 130, but may instead utilize one or more fault localization modules 136A-136B of the localization devices 110A-110B to perform the pipeline fault localization. In such embodiments, one localization device (e.g., 'B' 110B) will transmit, at dotted circle '5', its time value 164B through an auxiliary communications link 160 to the other localization device (e.g. 'A' 110A). In this embodiment, localization device 'A' 110A retains its determined time value and utilizes the time value 164B received from localization device 'B' 110B to, at dotted circle '6', calculate the estimated physical location of the pipeline fault 128. In an embodiment, both of localization devices 110A-110B exchange their respective determined time values using the auxiliary communication link 160, and the fault localization modules 136A-136B each calculate an estimated physical location of the pipeline fault 128. In some embodiments there are more than two such localization devices, each including a fault localization module 136B and configured to communicate their respective determined time values of detecting the fault signature to the other localization devices, and each configured to utilize two or more timing values for determining the fault location.

In the embodiment of the invention depicted in FIG. 1, each localization device 110A-110B may optionally be configured to transmit and receive failure detection traffic timing values 120A-120B (e.g., timestamps, values belonging to a sequence, etc.) through the pipeline segment 119 toward the other localization device using transmission modules 140A-140B and receiving modules 142A-142B. In embodiments utilizing this optional configuration, each fault localization module 136A-136C may be configured to rely upon one or more (162A, 162B) of these timing values 120A-120B when calculating the estimated physical location of the fault 128. For example, in one embodiment the pipeline segment 119 is metallic and carries a dielectric fluid as an electromagnetic waveguide in its own right, such that electromagnetic signals can be transmitted bi-directionally between the localization devices 110A-110B. Further detail regarding the possible types and uses of failure detection traffic is presented in FIG. 3 and below in that figure's supporting textual description.

Figure 2:
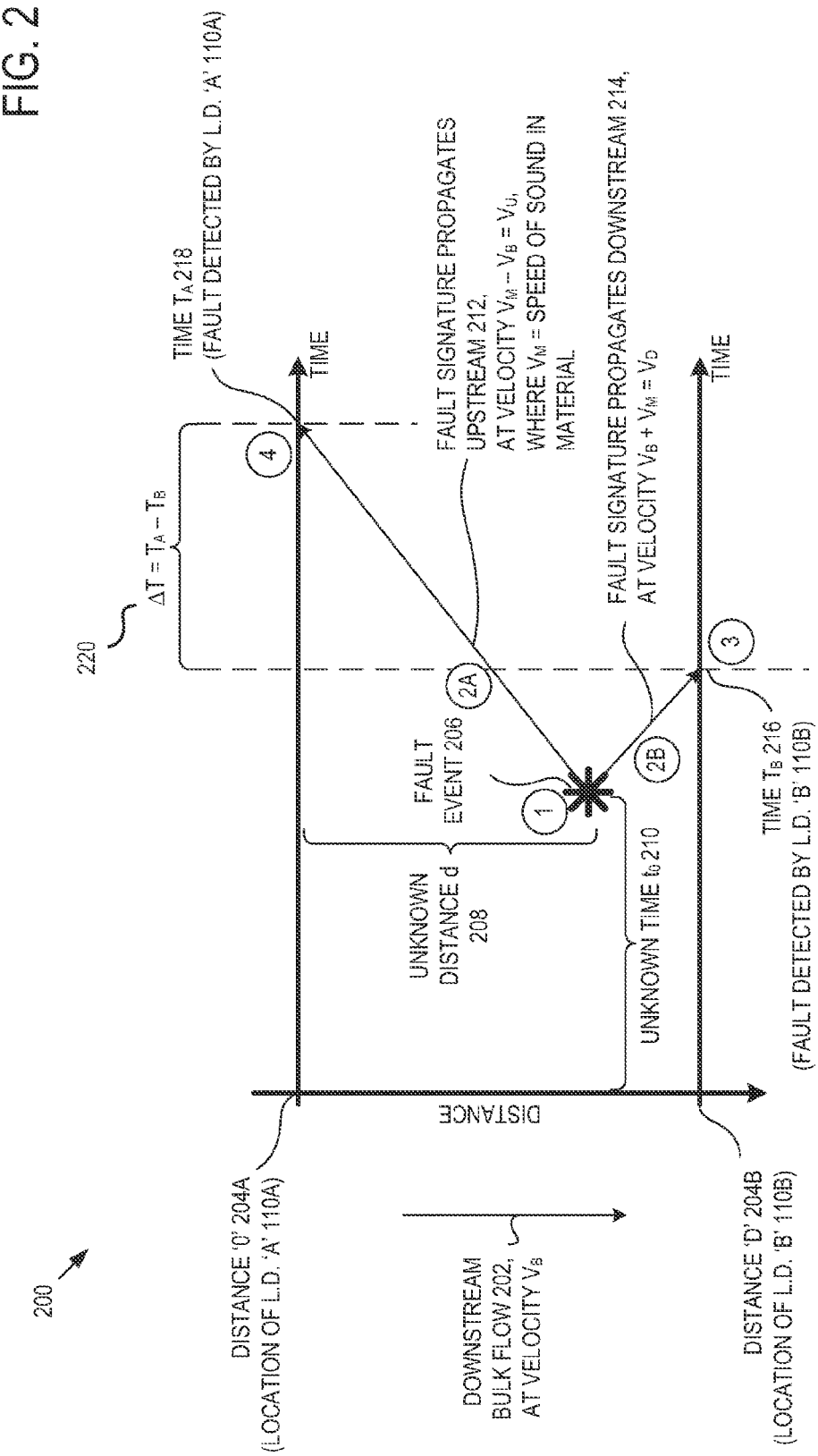
FIG. 2 illustrates the underlying principles of a system for localizing faults based upon time values related to the detection of fault signatures of the faults according to an embodiment of the invention.

FIG. 2 illustrates the underlying principles of a system 200 for localizing faults based upon time values related to the detection of fault signatures of the faults according to an embodiment of the invention.

In the depicted embodiment, localization devices 110A-110B are located at a reference distance '0' 204A and known distance 'D' 204B, respectively. Within the pipeline segment 119, a flow of matter 202 is present, at known velocity $V_B$, in the direction of increasing distance 'D', represented as the downward direction in FIG. 2. The speed of sound in the medium is also known, here designated as $V_M$.

Circle '1' illustrates the occurrence of a failure (e.g., fault event 206) of the pipeline at some unknown time $t_0$ 210 and some unknown distance 'd' 208 from the localization device 'A' 110A. According to an embodiment of the invention, a purpose of the present invention is to learn the value of 'd' 208, which is equivalent to the pipeline fault length 'A' 151A illustrated in FIG. 1. It will be recognized that the position 'd' 208 of the fault, relative to the arbitrary location '0' 204A of the localization device 110A, can be readily translated into any other distance or geographic measure, according to known distance or mapping relationships.

The fault event 206 may generate an acoustic wave, which may travel through the bulk matter 202 flowing through the pipeline. Circle '2B' illustrates the propagation 214 of such a wave in the downstream direction at velocity $V_D = V_B + V_M$. At circle '3', the wave reaches localization device 110B, which recognizes the wave as matching a fault signature and in response records the time $T_B$ of detection 216.

In similar fashion, the acoustic wave propagates 212 upstream (circle '2A') at upstream velocity $V_U=V_M-V_B$, and arrives (circle '4') at localization device 110A, which recognizes the wave as matching a fault signature and in response, records the arrival time $T_A$ 218.

It is to be understood, although not depicted in FIG. 2, that by way of some communications medium (e.g., an auxiliary communications link 160 or other communications link), $T_A$ and $T_B$ are reported to a fault localization module (e.g., one or more of 136A-136C), which is also not shown in this figure. As illustrated in FIG. 1, a variety of possibilities exist for the location of the fault localization module(s) 136A-136C, and the communications thereto.

The fault localization module (e.g. 136C), utilizing times $T_A$ and $T_B$ of fault detection reported by the localization devices 110A-110B, is configured to determine the location 'd' 208 of the fault. In various embodiments, this determination also utilizes one or more pieces of information describing the pipeline segment 119 and/or the matter flowing through the pipeline segment 119. For example, the determination may utilize one or more of a propagation velocity of the matter 202 transmitted through the pipeline, a propagation velocity of acoustic waves transmitted through the matter in the pipeline or the walls of the pipeline, a length of the pipeline between the first location (e.g., distance '0' 204A) and the second location (e.g., distance 'D' 204B), and an acoustic wave propagation delay of the pipeline between the first location and the second location.

In an embodiment, the fault localization module (e.g. 136C) utilizes the times $T_A$ and $T_B$ of fault detection, the distance 'D' between localization devices (i.e. the distance between location '0' 204A of the localization device 'A' 110A and location 'D' 204B of the localization device 'B' 110B), the velocity $V_B$ of the bulk flow of matter 202 through the pipeline, and the velocity of propagation of sound in the bulk matter. This determination is based on the relationship:

$$\text{distance} = \text{velocity} * \text{time} \tag{1}$$

From the vantage point of localization device 110A:

$$d = V_U(T_A - t_0) = V_U T_A - V_U t_0 \tag{2}$$

$$t_0 = (V_U T_A - d)/V_U \tag{3}$$

From the vantage point of localization device 110B:

$$D - d = V_D(T_B - t_0) \tag{4}$$

$$d = D - V_D(T_B - t_0) = D - V_D T_B + V_D t_0 \tag{5}$$

$$t_0 = (d - D + V_D T_B)/V_D \tag{6}$$

To eliminate the unknown time $t_0$, equations (3) and (6) are equated:

$$t_0 = (V_U T_A - d)/V_U = (d - D + V_D T_B)/V_D \tag{7}$$

$$V_D(V_U T_A - d) = V_U(d - D + V_D T_B) \tag{8}$$

$$V_D V_U T_A - V_D d = V_U d - V_U D + V_D V_U T_B \tag{9}$$

$$V_U d + V_D d = V_U D + V_D V_U T_A - V_D V_U T_B \tag{10}$$

$$d = (V_U D + V_D V_U \Delta T)/(V_U + V_D) \tag{11}$$

Where $\Delta T$ is simply $T_A - T_B$, which illustrates that for the purposes of fault localization, the absolute clock times $T_A$ and $T_B$ are not significant, but their difference ($\Delta T$) 220 is.

In some embodiments, the acoustic wave in a pipeline propagates through the walls of the pipeline itself. In such a case, the propagation velocity of the acoustic wave is independent of the bulk flow rate, and has velocity $V_W$ in the wall material of the pipeline. In such embodiments, the localization devices 110A-110B may be configured to detect two fault signatures from the same failure: one through the fluid, the other through the walls of the pipeline.

In embodiments when upstream and downstream acoustic waves propagate at the same velocity $V_W$ in the pipeline walls, equation (11) is modified to become a new equation (12):

$$d = (V_W D + V_W^2 \Delta T)/2V_W = \tfrac{1}{2}(D + V_W \Delta T) \tag{12}$$

Thus, in some embodiments of the invention, each localization device (e.g. 110A) is configured to determine time information values related to a plurality of detected fault signatures, and report some or all of the time information values to the fault localization module (e.g. 136C) to be used to determine the fault location. In some embodiments, the fault localization module 136C utilizes detection times of a particular fault signature (e.g., based upon a wave in the matter transported through the pipeline, a wave travelling through the walls of the pipeline, a change in flow or pressure of the matter in the pipeline, etc.) from each of the localization devices 110A-110B to generate a first estimated fault location, and then utilizes detection times of a different fault signature (e.g., based upon an acoustic wave propagated through the walls of the pipeline) from each of the localization devices 110A-110B to generate a second estimated fault location. In an embodiment where the fault localization module 136C generates a plurality of estimated fault locations based upon time values of different fault signatures, each of the estimated locations may be presented to a user, or the estimated fault locations may be averaged (non-weighted, or weighted) and presented to a user as a way of improving the estimate of the fault location.

In some embodiments, the fault signature in a pipeline may be evidenced by a sudden drop in pressure, possibly accompanied by a sudden increase in flow rate as seen by the upstream localization device 110A, or a sudden decrease in flow rate as seen by the downstream localization device 110B. However, other such fault signatures are known to those of skill in the art, and thus this list is exemplary and non-exhaustive.

While the preceding description contemplates a pipeline carrying a fluid, either gaseous or liquid, the same analysis applies to electrical power transmission lines, wherein the velocity of propagation of the fault signature is independent of direction and equal to the propagation velocity of electromagnetic energy in the transmission line medium.

As described later herein, embodiments of the invention allow for fault localization in electrical transmission lines. In an electrical transmission line, according to embodiments of the invention, a fault signature may appear at a localization device as a sudden change of voltage, possibly accompanied by a sudden increase in current as observed at the upstream localization device 110A, or a sudden decrease in current as observed at the downstream localization device 110B. It is understood that at least the upstream breaker would trip, and then re-close, and possibly trip again, with each such action generating additional perturbations on the line. Fault signature analysis algorithms may be integrated into this operational model with techniques understood by those skilled in the art. Thus, in various embodiments of the invention, the localization device 110 of an electrical transmission line may be adapted to monitor or measure voltage and current absolutely or differentially between any of the phases, or between any of the phases and earth ground. Further detail regarding fault localization is described later herein in FIGS. 8-10 and their associated text descriptions.

Figure 3:
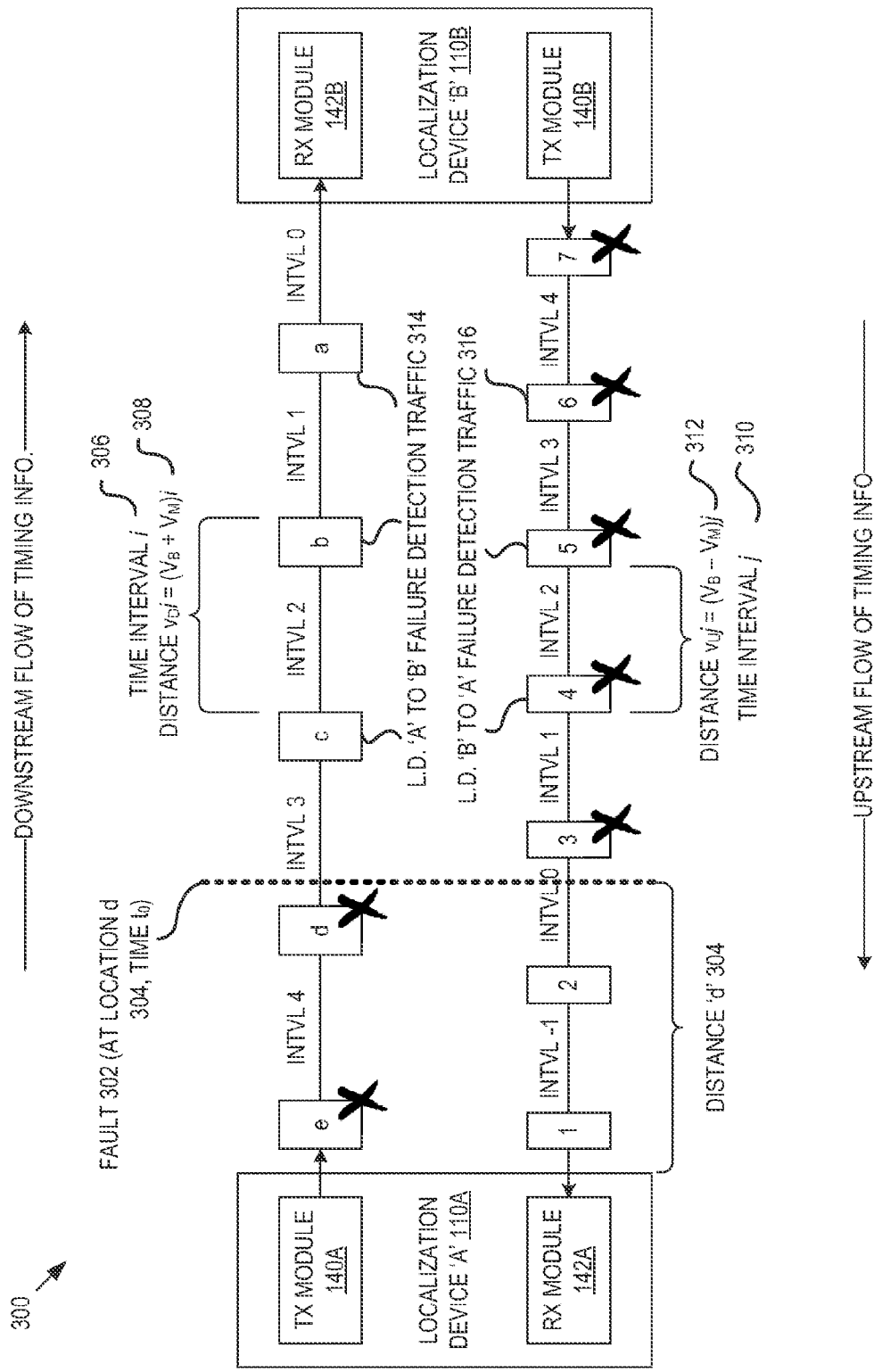
FIG. 3 illustrates the underlying principles of a system for localizing faults utilizing failure detection traffic according to an embodiment of the invention.

FIG. 3 illustrates the underlying principles of a system 300 for localizing faults utilizing failure detection traffic according to an embodiment of the invention. In this depicted embodiment, the localization devices 110A and 110B are adapted to transmit (using a transmission module 140A-140B) and receive (using a receiving module 142A-142B) time stamps, or aliases thereof, between themselves as failure detection traffic (e.g., 120A-120B). In an embodiment, each localization device 110A-110B transmits a time stamp (or alias) periodically, with period 'i' (e.g., 306, 310). In FIG. 3, downstream failure detection traffic 314 values (e.g., time stamps) are illustrated as lettered boxes, 'a'-'e', while upstream failure detection traffic 316 (e.g., time stamps) values are illustrated as numbered boxes, '1'-'7'. The downstream flow of failure detection traffic 314, from localization device 110A to localization device 110B, has a greater propagation velocity, suggested by the expanded size of the time stamp boxes 'a'-'e', and their greater spacing (e.g., 308) along the line, as compared to the more compact spacing (e.g. 312) of the upstream flow of failure detection traffic 316 represented by time stamp boxes '1'-'7'. For simplicity of explanation, it is stipulated, without loss of generality, that the time reference frames at localization devices 'A' 110A and 'B' 110B are the same, and that the interval start times are aligned at the localization device points. However, in other embodiments of the invention, this is not necessarily true, and fault localization calculations may account for differences in time references by the localization devices 110A-110B and differences in interval start times.

To further illustrate the difference in propagation velocity, FIG. 3 illustrates the interval numbers in the two directions. In the downstream direction, timestamp 'a' corresponds to interval '0', and will be the next timestamp received by localization device 'B' 110B. In the upstream direction, timestamp '3' was transmitted by localization device 'B' 110B at the same time downstream timestamp 'a' was transmitted, but as can be seen, it will not arrive at localization device 'A' 110A until 2 preceding timestamps have arrived.

As illustrated in FIG. 3, a fault 302 occurs at unknown location 'd' 304 and unknown time $t_0$. Thus, in the downstream direction, timestamps 'd' and 'e' will never be received by localization device 110B, as indicated by the X in their symbols. Similarly, it is also apparent that timestamps '3'-'7' will never be received by localization device 110A.

Because the reference frames are synchronized, however, localization device 'B' 110B can determine that the fault occurred during interval '3', and can estimate a detection time $T_B$, for example at the midpoint of interval '3'. In like manner, localization device 'A' 110A can determine that the fault occurred during interval '0', and can likewise estimate a detection time $T_A$. In an embodiment, detection times $T_A$ and $T_B$ can be utilized by a fault localization module (e.g., 136C) to calculate an estimated physical location of the fault 128 as described above in FIG. 2.

From FIG. 3, it will be appreciated that estimates of $T_A$ and $T_B$ introduce additional uncertainty in the ultimate estimate of the distance 'd' 304 (i.e., estimated physical location of the fault). These uncertainties may be reduced to acceptable limits by reducing the interval between the transmission of timestamps or their equivalent. In an embodiment, timestamp-based analysis may be combined with acoustic-wave analysis to improve on the accuracy of either method as used in isolation.

Although FIG. 3 is initially described in terms of discrete timestamps or their equivalent, it is also understood that progressive transmissions of PRBS, one or a few bits at a time, will likewise establish a reference interval that can be used in the same way.

FIG. 3 pictorially exemplifies the consequences of differing propagation velocities in the upstream and downstream direction. In the case where localization devices 110A-110B transmit acoustically-encoded signals to each other, the flow velocity $V_B$ causes a Doppler shift in the received frequencies that is either positive or negative according to the direction of transmission and the direction of flow.

An embodiment of the invention utilizes knowledge of the flow velocity $V_B$ to adjust its receive filters such that it properly receives the signal from the remote localization device.

Alternatively, an embodiment may adapt its filters to properly receive the signal using a feedback loop whose construction will be straightforward to those skilled in the art. The degree of adaptation required may be combined with foreknowledge of the frequencies in the transmitted signal to measure the Doppler shift and thereby the (directional) velocity $\pm V_B$ of the matter flow.

Figure 4:
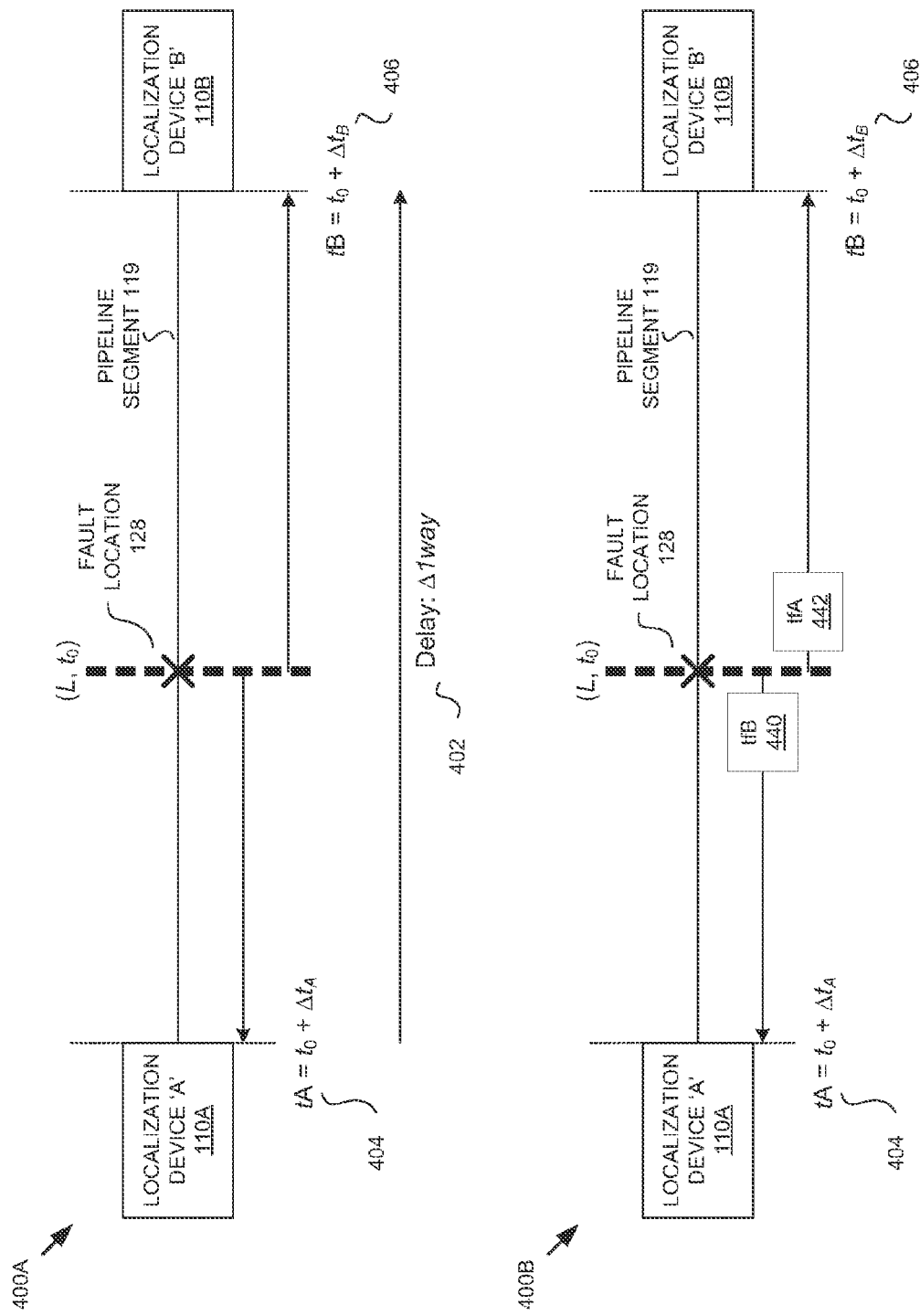
FIG. 4 illustrates an approach for localizing pipeline faults utilizing time value information transmitted between localization devices according to one embodiment of the invention.

FIG. 4 illustrates an approach for localizing pipeline faults utilizing time value information transmitted between localization devices according to one embodiment of the invention, assuming the speed at which the fault-detection characteristics of matter travels toward the localization devices is approximately equal in each direction. FIG. 4 includes a pipeline segment 119 carrying injected fault detection traffic in each direction between localization device 'A' 110A and localization device 'B' 110B. Each localization device 110A-110B includes a time of day clock module (not illustrated) that is synchronized to a common frame of reference. In certain embodiments of the invention, this synchronization is provided through one of Network Time Protocol (NTP), Precision Time Protocol, or Global Positioning System (GPS).

At 400A, at an unknown location "L" and time "t0", the pipeline segment 119 has a failure. Evidence of the failure, which will match a fault signature, travels in both directions of the pipeline segment 119. Repair of the pipeline is facilitated by determining the location "L" of the failure 128.

The consequence of the failure will propagate to localization device 'A' 110A, where it is observed at time "tA"="t0"+"ΔtA", indicated by reference numeral 404. Likewise, the failure is observed at localization device 'B' 110B at time "tB"="t0"+"ΔtB", indicated by reference numeral 406. The location of the failure 128 can be determined by a fault localization module 136 (not illustrated in FIG. 4, but may exist as part of one or both of the localization devices 110A-110B, or as part of a separate management device 130) from the values of "ΔtA" and "ΔtB" through the calculation of simple proportions.

In one embodiment, if each localization device transmits a continuing series of time stamps to the other localization device over the pipeline segment 119, there will be one final time stamp at each end that crosses the failure locus immediately prior to the failure. This final time stamp will be received at the far end of the pipeline segment 119 by the other localization device, which can derive Δt (A or B) by subtracting the received final time stamp value from its own current time. In some embodiments, the final time stamp (or time alias) received by one or both of the localization devices 110A-110B are transmitted 162A-162B to the fault localization module 136C to be used for calculating the estimated physical location of the fault.

In another embodiment, the value of "t0" is determined as a step in a derivation of "Δt". The one-way delay 402 of the pipeline ("Δ1way" 402) can be calculated or measured during installation or operation of the pipeline and possibly verified/updated from time to time during normal operation thereafter.

Assuming that the "Δ1way" value 402 is known, then:

$$\Delta 1\text{way} = \Delta tA + \Delta tB$$

Then, by substitution:

$$\Delta 1\text{way} = (tA - t0) + (tB - t0) = tA + tB - (2*t0)$$

Therefore, $$t0 = 0.5*(tA + tB - \Delta 1\text{way})$$

So:

$$\Delta tA = tA - t0 = tA - 0.5*(tA + tB - \Delta 1\text{way}) = 0.5*(tA - tB + \Delta 1\text{way})$$

$$\Delta tB = tB - t0 = tB - 0.5*(tA + tB - \Delta 1\text{way}) = 0.5*(tB - tA + \Delta 1\text{way})$$

The previous equations do not require time stamps, but assume that localization devices 110A and 110B are mutually synchronized, that is, that their clocks agree, and that the velocity of propagation is the same in each direction.

As noted above, in an embodiment of the invention each localization device 110A-110B transmits a continuing series of time stamps, thereby avoiding the need for mutual synchronization. For example, consider the example illustrated at 400B wherein the clock domains of localization device 'A' 110A and localization device 'B' 110B differ by some unknown correction factor "Toffset." Each localization device 110A-110B transmits time stamps toward the other. In the direction toward localization device 'A' 110A, a final time stamp "tfB" 440 passes the fault location 128 immediately prior to the failure. Likewise, a final time stamp "tfA" 442 passes the fault location 128 in the direction from localization device 'A' 110A toward localization device 'B' 110B.

At localization device 110A, the time stamp "tfB" 440 is received at local time "tA", the instant at which localization device 'A' 110A observes the occurrence of the failure. In the timing epoch of localization device 'A' 110A, tfB should be corrected by adding "Toffset", which is unknown.

At localization device 'B' 110B, the final time stamp "tfA" 442 is received at local time "tB", also in incompatible timing domains.

However, if all four values are available at a single analysis point, such as at a fault localization module 136, the time stamps may be relocated into their own clock domains and the deltas may be computed separately without the need to know the offset between domains using the following equations:

$$\Delta tA(\text{true}) = tA - tfA$$

$$\Delta tB(\text{true}) = tB - tfB$$

With the relative position of the fault 128 known in the time domain from the perspective of both localization device 'A' 110A and localization device 'B' 110B, the physical location of the fault may be determined through reference to auxiliary information such as link length or Geographic Information Systems (GIS) data, and presented to repair personnel as a distance, map coordinates, or in any other form that is meaningful and helpful.

It is to be understood that the accuracy and resolution of the failure location estimate are affected by a number of factors, including synchronization mismatches between the localization devices 110A-110B, uncertainty in the precise instant of a failure, a non-zero time from the beginning of a failure until complete failure, the repetition rate of transmitted time stamps, the time required to send a time stamp at a finite data rate, random errors, and other factors. Those of skill in the art will be able to assess the relative effect of each factor and determine whether the ultimate fault location objective can nevertheless be achieved.

Embodiments of the invention do not need to rely upon time values such as timestamps or generated clock time values, but may instead utilize sequence numbers, which represent time stamps as aliases. Sequence numbers may comprise simple counters, pseudo-random binary sequences (PRBS), or other values, subject only to the need to be unambiguous within the transit time of signals transmitted between the localization devices 110A-110B. In an embodiment, timestamp aliases may allow for brevity in representation. For example, it may require 32 bits to represent a time of day, while a 12-bit counter may suffice to produce unambiguous aliases in the pipeline. A PRBS may have the benefit that only one bit need be transmitted at a time, exploiting the property that the PRBS is known to be non-repeating and therefore unambiguous within its length. There may be benefit in transmitting several bits of a PRBS in each transmission, for example if the modulation format used for transmission generates complex multi-tone symbols. In another embodiment, a gray code sequence of aliases may be selected, with the property that only one bit changes between any given value and the next, thereby reducing uncertainty in receiving the intended value.

When timestamp aliases are received at a localization device 110A-110B, an embodiment first converts them to actual timestamps, using prearranged and known properties of the selected alias design. Subsequent analysis occurs in the time domain according to the analyses presented earlier.

Figure 5:
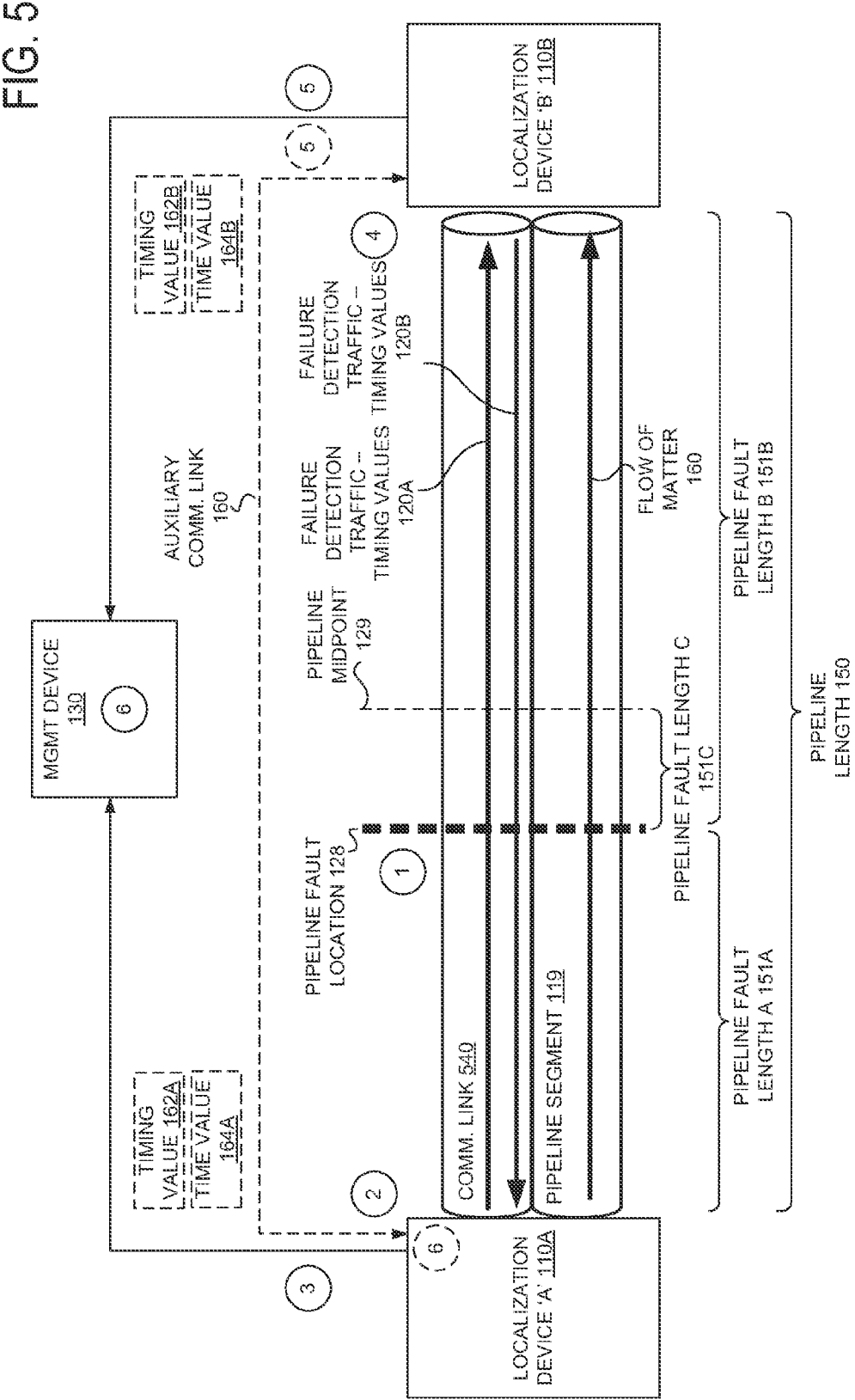
FIG. 5 illustrates a system configuration utilizing a communications link coupled to a pipeline for localizing faults in the pipeline according to an embodiment of the invention.

FIG. 5 illustrates a system configuration utilizing a communications link 540 coupled to a pipeline segment 119 for localizing faults in the pipeline according to an embodiment of the invention. This system configuration is similar to the system configuration of FIG. 1, except the failure detection traffic 120A-120B (e.g., timestamps, sequence values/time aliases, etc.) is instead transmitted over a communications link 540 coupled to the pipeline segment 119 instead of through the pipeline segment 119 itself. Thus, instead of needing to transmit this traffic 120 using the pipeline segment 119, it can be transmitted on a separate channel using a (dedicated or non-dedicated) communications link 540, and thereby can function similar to the configuration presented in FIG. 1. Such an embodiment may offer benefits including ease of maintenance, reduced time required for detection, improved detection accuracy (as signals transmitted on the communications link 540 may more clearly indicate the existence of a fault), decreased system complexity, etc. The communications link may use electrical or optical, rather than acoustic, signals, thereby removing the speed of sound as a consideration.

In one embodiment, the communications link 540 is coupled to the exterior of the pipeline segment 119 (as depicted), but in other embodiments the communications link 540 may be coupled to the pipeline segment 119 by being attached to an inner wall of the pipeline segment 119, located within a wall of the pipeline segment 119, or simply run through the pipeline segment 119. For example, in an embodiment of the invention, an optical link 540 is embedded within the pipeline segment 119, with mirrors utilized if necessary to reflect the optical signal at curves and bends. This embodiment may be especially suitable for use inside pipelines intended to carry matter that is essentially transparent to the wavelength of the optical channel. In some embodiments, the communications link 540 is not in contact with the flow of matter 160 transported through the pipeline segment 119, but instead is sensitive to the matter such that any exposure to the matter (that is, from a fault in the pipeline segment 119) will cause the communications link 540 to have a degradation of signal quality and/or a physical fault itself. For example, in an embodiment the communications link 540 is an electromagnetic messenger link run along the same route as the pipeline and tightly coupled into the pipeline itself. In an embodiment, the electromagnetic messenger link is in contact with (or at partially or wholly made of) a chemical composition sensitive to the matter being transmitted through the pipeline such that a failure of the pipeline is highly likely to also damage or destroy the messenger link at the same point.

In addition to the communications link 540, the system of FIG. 5 may also include an auxiliary communications link 160 to allow the fault localization modules 136A-136B of the localization devices 110A-110B to transmit information (e.g. transmitted/received timing values, timestamp information, etc.) to one another for the purpose of fault localization. Similarly, the system of FIG. 5 may also include some other communications link or use some other communications medium to report the information to a management device 130.

Figure 6:
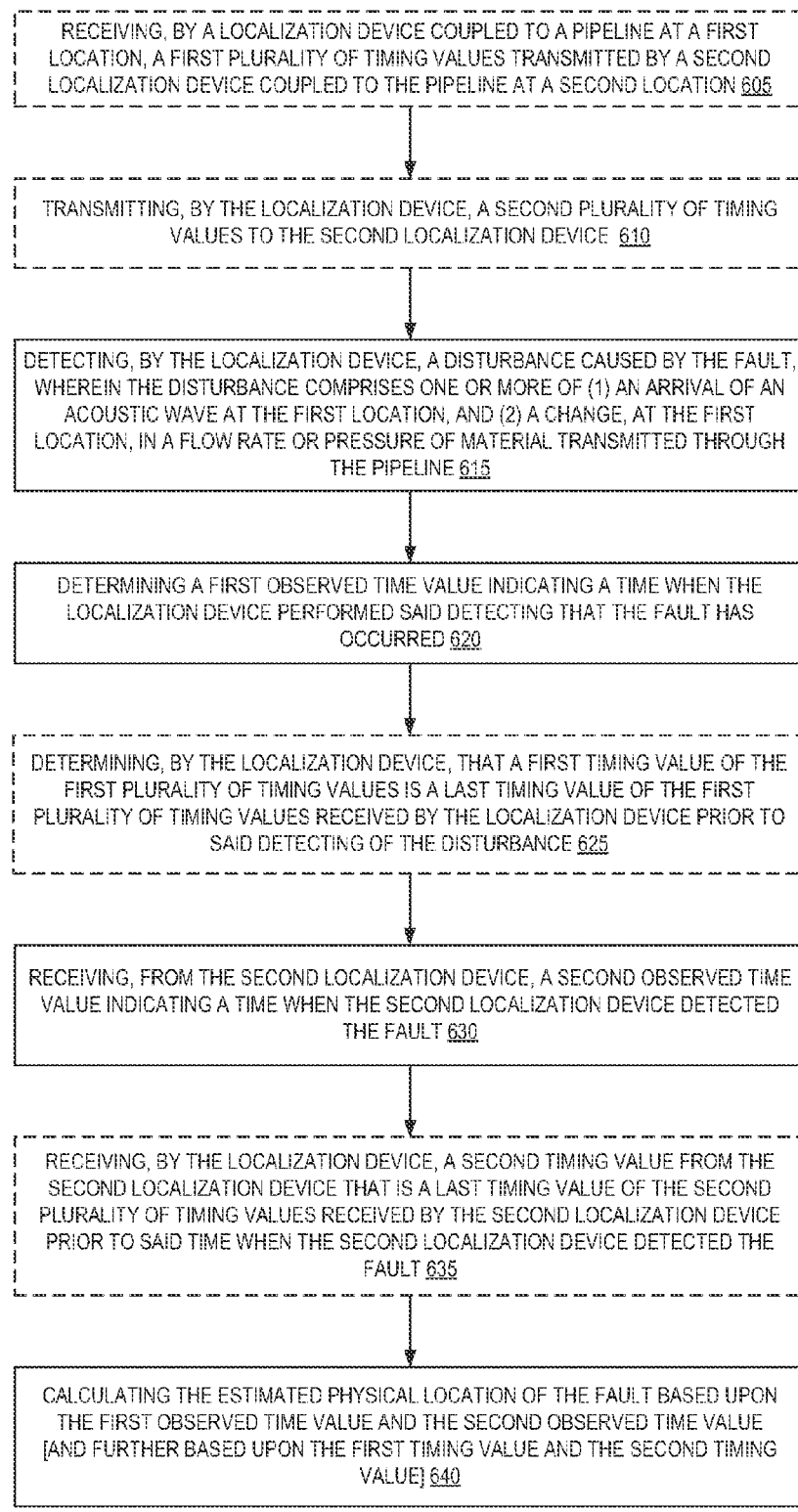
FIG. 6 illustrates a flow for determining an estimated physical location of a fault in a pipeline by a localization device coupled to the pipeline at a first location according to an embodiment of the invention.

FIG. 6 illustrates a flow 600 for determining an estimated physical location of a fault in a pipeline by a localization device coupled to the pipeline at a first location according to an embodiment of the invention. The boxes with solid outlines illustrate a flow 600 utilizing the times that the localization devices detect a fault signature to calculate the estimated physical location of the fault, and the boxes with the dashed/dotted outlines include optional steps to also utilize timing values transmitted between the localization devices when calculating the estimated fault location.

At block 605, the flow optionally includes receiving, by a localization device, a first plurality of timing values transmitted by a second localization device coupled to the pipeline at a second location. The timing values may be different types, such as timestamps or sequence values/timestamp aliases. In certain embodiments, the timing values are acoustically encoded bits, and in some embodiments the timing values are sequences of single tones and/or complex multi-tones. At 610, the flow optionally further includes transmitting, by the localization device, a second plurality of timing values to the second localization device. The second plurality of timing values may be of the same type as the first plurality of timing values, or may be of a different type, depending upon the embodiment.

The flow, at block 615, includes detecting, by the localization device, a disturbance caused by the fault. The disturbance may be an arrival of an acoustic wave at the first location, or a change, at the first location, in a flow rate or pressure of the matter transported through the pipeline. In an embodiment, the detection of the disturbance occurs when a disturbance matches a fault signature. Next, the flow includes determining a first observed time value indicating a time when the localization device performed said detecting of the disturbance 620.

Optionally, at 625, the flow includes determining, by the localization device, that a first timing value of the first plurality of timing values is a last timing value of the first plurality of timing values received by the localization device prior to the detecting of the disturbance.

The flow 600 continues with receiving 630, from the second localization device, a second observed time value indicating a time when the second localization device detected the fault. In some embodiments, the second localization device detects the fault when it detects a disturbance, which matches a fault signature. The disturbance may be an arrival of an acoustic wave at the second location, or a change, at the second location, in a flow rate or pressure of the matter transported through the pipeline. The disturbance at the second location may be different from the disturbance at the first location.

Optionally, at 635, the flow includes receiving, by the localization device, a second timing value from the second localization device that is a last timing value of the second plurality of timing values received by the second localization device prior to said time when the second localization device detected the fault. This second timing value, in an embodiment, is transmitted from the second localization device to the localization device over an auxiliary communications link. In an embodiment, the auxiliary communications link is a wireless connection.

At 640, the flow includes calculating the estimated physical location of the fault based upon the first observed time value and the second observed time value. In an embodiment, the calculation is also based upon one or more known properties of the pipeline or the matter being transported through the pipeline. Optionally, the calculating is further based upon the first timing value and the second timing value.

In an embodiment, the estimated physical location of the fault is transmitted to a computing device to notify a user of the estimated physical location of the fault. In an embodiment, the estimated physical location of the fault is displayed to a user, through one or more of a projector, monitor, television, computing device display/screen, physical print-out, etc.

FIG. 7 illustrates a flow 700 for determining an estimated physical location of a fault in a pipeline by a computing device according to an embodiment of the invention. In this flow 700, the computing device may be distinct from the localization devices, thereby removing the necessity for the localization devices to be in communication with each other and for (at least) one of the localization devices to be able to perform fault localization calculations.

At 705, the flow begins with the computing device receiving, from a first localization device coupled to the pipeline at a first location, a first observed time value. The first observed time value indicates a time when the first localization device detected a disturbance caused by the fault. The disturbance may be one or more of an arrival of an acoustic wave at the first location, or a change, at the first location, in a flow rate or pressure of the matter transmitted through the pipeline. Optionally, at 710, the computing device receives, from the first localization device, a first timing value that is a last timing value of a first plurality of timing values received by the first localization device from the second localization device prior to said time that the first localization device detected the disturbance.

At block 715, the computing device receives, from a second localization device coupled to the pipeline at a second location, a second observed time value. The second observed time value indicates a time when the second localization device detected the fault. In some embodiments, the second localization device detects the fault when it detects a disturbance, which matches a fault signature. The disturbance may be an arrival of an acoustic wave at the second location, or a change, at the second location, in a flow rate or pressure of the matter transported through the pipeline. The disturbance at the second location may be different from the disturbance at the first location. Optionally, at 720, the computing device receives, from the second localization device, a second timing value that is a last timing value of a second plurality of timing values received by the second localization device from the first localization device prior to said time that the second localization device detected the fault.

At 725, the computing device calculates the estimated physical location of the fault based upon the first observed time value and the second observed time value. In an embodiment, the calculation is also based upon one or more known properties of the pipeline or the matter being transmitted through the pipeline. Optionally, the calculation is further based upon the first timing value and the second timing value. In an embodiment, the estimated physical location of the fault is transmitted to a second computing device to notify a user of the estimated physical location of the fault. In an embodiment, the estimated physical location of the fault is displayed to a user, through one or more of a projector, monitor/television/screen of or utilized by a computing device, physical print-out, etc.

Localizing Faults in Electrical Power Transmission Lines

Just as in pipelines, a fault within an electrical power transmission line can be catastrophic to those who depend upon it, and the re-establishment of service must occur as quickly as possible. Additionally, similar to pipelines, electrical power transmission lines can be many miles in length and the faults therein can be difficult to quickly localize.

In one embodiment of the invention, fault localization in electrical power transmission lines utilizes local timing values (respectively captured and/or generated at the time of fault detection) taken at two different geographic locations on the line. Thus, localization devices may be configured to detect a fault signature such as an electromagnetic surge (e.g., change in voltage, change in current, etc.) that may accompany a sudden, clean (i.e., complete) failure on the line, and report or utilize local timing information associated with such sudden failures. However, some embodiments may utilize, in addition to the local timing values generated by each localization device, timing information transmitted over the electrical power transmission lines between the localization devices (e.g., using power-line telemetry, a well-known and widely-deployed technology), which may assist in localizing faults for non-sudden and/or non-complete failures resulting from occurrences such as lightning strikes and falling trees. In an embodiment, the localization devices are (or include) electronic computing devices, as defined above.

Figure 8:
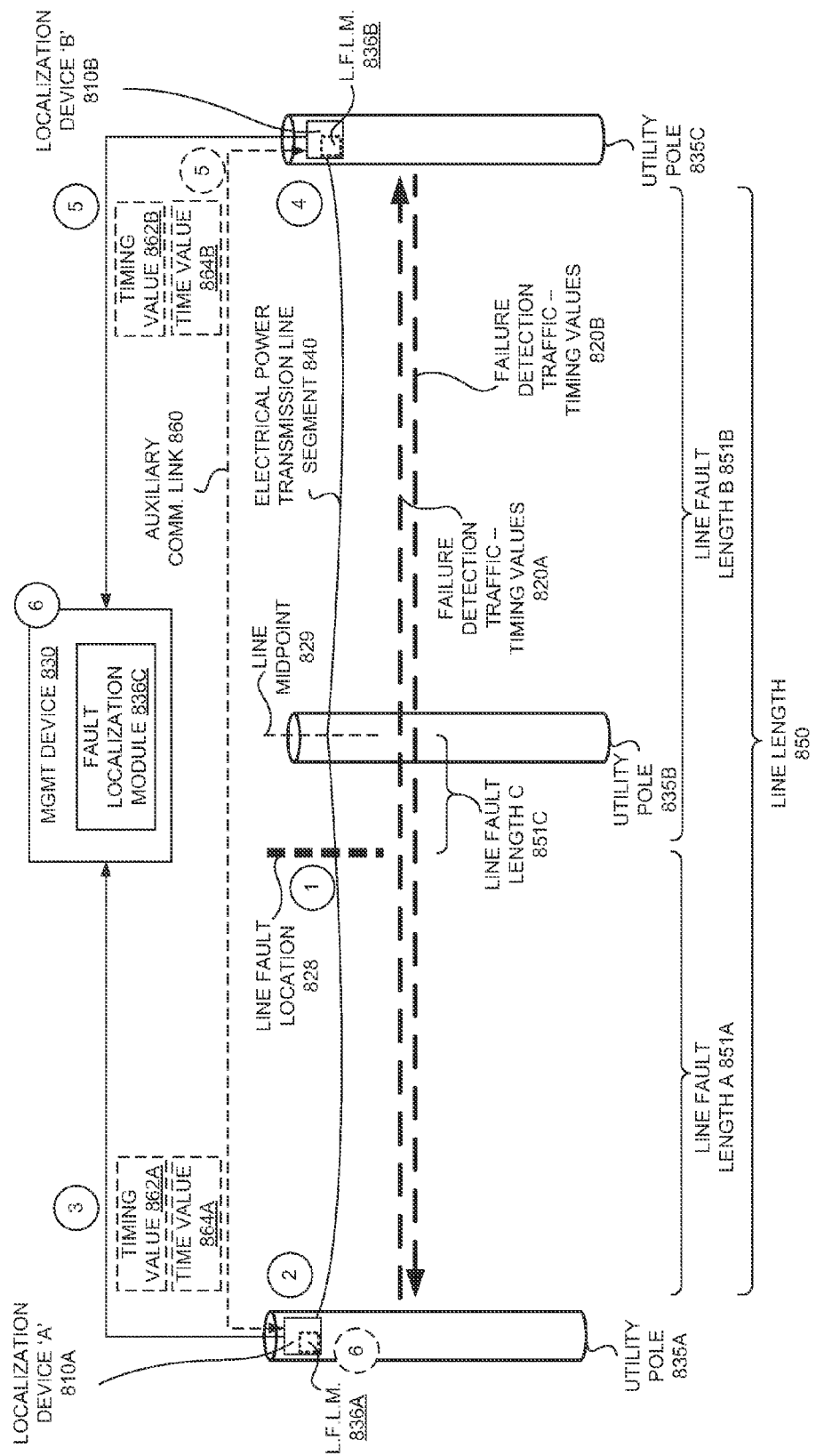
FIG. 8 illustrates a system configuration for localizing faults in an electrical power transmission line according to an embodiment of the invention.

FIG. 8 illustrates a system configuration for localizing faults in an electrical power transmission line 840 according to an embodiment of the invention. In this embodiment, the electrical power transmission line 840, which may be optionally connected to one or more utility poles or towers 835A-835C, has a line fault at a particular location 828 at circle '1'. In an embodiment, a fault signature of an electromagnetic surge is detected at circle '2' at localization device 'A' 810A (which is similar to the localization devices 110A-110B of FIG. 1 and may include similar modules [e.g., link fault localization modules 836A-836B] and perform similar functions), which will determine a local time value of this detection. In embodiments where a management device 830 ultimately calculates the estimated fault location 828, the localization device 'A' 810A transmits the local time value 864A to the management device 830 at circle '3' using a wired or wireless communication link or channel. The localization device 'A' 810A (and localization device 'B' 810B), in some embodiments, synchronizes itself to a particular time frame of reference (e.g., using a GPS system, NTP system, etc.), but in other embodiments the management device 830 adjusts the reported local time values to place them in a common time frame of reference. In embodiments where one of the localization devices (e.g., 810A) calculates the estimated line fault location 828, the localization device 'A' 810A preserves the determined local time value corresponding to the time of the fault detection, either in short-term or long-term memory or other storage.

At circle '4', the electromagnetic surge will have traveled the length of line fault length 'B' 851B and will be detected as matching a fault signature by localization device 'B' 810B, which will determine a local time value corresponding to the time when it detected the fault. In an embodiment utilizing a management device 830 for the calculation of the estimated line fault location 828, at circle '5' the localization device 810B will transmit the local time value 864B to the management device 830, but in other embodiments where the localization device 'A' 810A is configured to calculate the estimated line fault location 828, the local time value is transmitted by the localization device 810B to the localization device 'A' 810A over an auxiliary communications link 860, which may be wired or wireless.

At circle '6', either the fault localization module 836C of the management device 830 or the localization device 'A' 810A will compute, based upon the local timing values from localization device 'A' 810A and localization device 'B' 810B as well as known properties of the electrical power transmission line 840 (e.g., a length 850 of the electrical power transmission line segment 840), the estimated physical location of the fault 828. This estimated physical location of the fault 828 may be a particular point (e.g., a geographic indication of the fault, such as a latitude and/or longitude, or an intersection or nearby geographic landmark), or may be one or more of a distance from one of the electrical sensors 810A-810B to the fault 828 (e.g., line fault length 'A' 851A, line fault length 'B' 851B) or from a line midpoint 829 to the fault 828 (e.g., line fault length 'C' 851C).

Similar to the embodiments described above with respect to the calculation of estimated physical fault locations in pipelines, the system of FIG. 8 may further utilize timing information (i.e., failure detection traffic) in addition to the local time values generated by the localization devices 810A-810B for localizing faults. Thus, in some embodiments, the localization devices 810A-810B each transmit failure detection traffic timing values 820A-820B over the electrical power transmission line 840 toward the other localization device, and may report one or more timing values 862A-862B to the fault localization module(s) 836A-836C calculating the estimated physical location of the fault 828. Further detail regarding the possible types and uses of failure detection traffic is presented above, including but not limited to FIG. 3 and its supporting textual description herein. It is understood that the high propagation velocity of electromagnetic signals, together with the comparatively low bandwidth of telemetry channels, may render the transmission of one or a few bits of a PRBS at a time especially advantageous.

Figure 9:
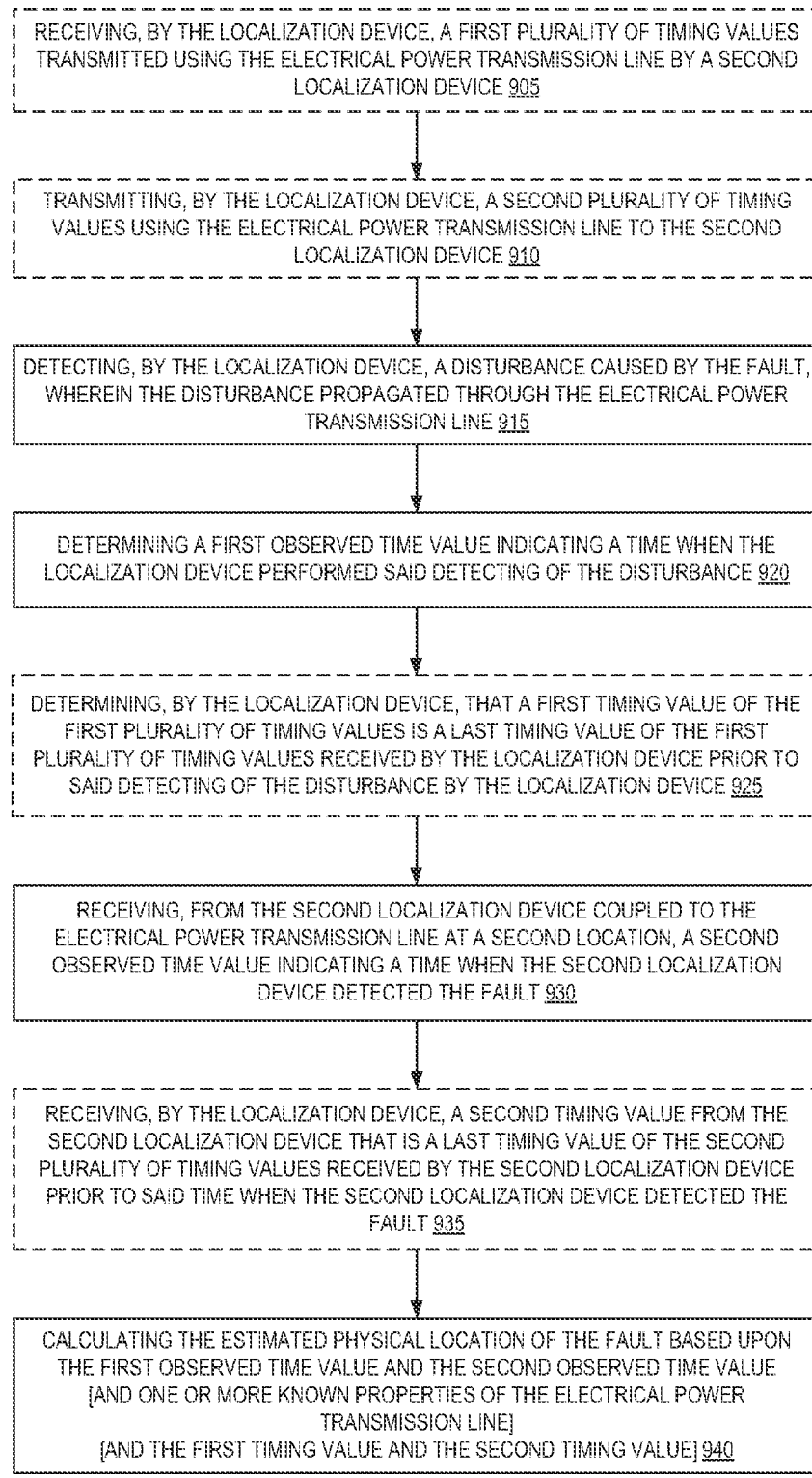
FIG. 9 illustrates a flow for determining an estimated physical location of a fault in an electrical power transmission line according to an embodiment of the invention.

FIG. 9 illustrates a flow 900 in a localization device coupled to an electrical power transmission line at a first location for determining an estimated physical location of a fault in the electrical power transmission line according to an embodiment of the invention.

In those embodiments of the invention utilizing timing information transmitted over the electrical power transmission line to calculate the estimated physical location of the fault, the localization device receives a first plurality of timing values transmitted using the electrical power transmission line by a second localization device 905 coupled to the line at a second location, and the localization device transmits a second plurality of timing values using the electrical power transmission line to the second localization device 910. In some embodiments, the timing values are timestamps, and in some embodiments the timing values are time aliases, such as PRBS values.

At block 915, the localization device detects a disturbance, caused by the fault, which has propagated through the electrical power transmission line. In an embodiment, the disturbance is a change in one or more of a current and voltage. At this point, at block 920, the flow includes determining a first observed time value indicating a time when the localization device detected the disturbance.

Optionally, in those embodiments of the invention utilizing timing information transmitted over the electrical power transmission line, at block 925 the flow includes determining, by the localization device, that a first timing value of the first plurality of timing values is a last timing value of the first plurality of timing values received by the localization device prior to said detecting of the disturbance by the localization device.

At block 930, the localization device receives, from the second localization device, a second observed time value indicating a time when the second localization device detected the fault. In an embodiment, the second localization device detects the fault by detecting the arrival of a disturbance at the second location. In an embodiment, the disturbance is one or more of a change in current and voltage of the electrical power transmission line.

Optionally, in those embodiments of the invention utilizing timing information transmitted over the electrical power transmission line, at block 935 the localization device receives a second timing value from the second localization device. The second timing value is a last timing value of the second plurality of timing values received by the second localization device prior to said time when the second localization device detected the fault.

Then, the localization device calculates the estimated physical location of the fault based upon the first observed time value and the second observed time value 940. In some embodiments, the calculation is also based upon one or more known properties of the electrical power transmission line. In an embodiment, the one or more known properties of the electrical power transmission line include one or more of a propagation velocity of electromagnetic waves transmitted using the electrical power transmission line and a length of the electrical power transmission line. In some embodiments of the invention, the calculation is further based upon the first timing value and the second timing value.

In an embodiment, the estimated physical location of the fault is transmitted to a computing device to notify a user of the estimated physical location of the fault. In an embodiment, the estimated physical location of the fault is displayed to a user, through one or more of a projector, monitor, television, computing device display/screen, physical print-out, etc.

Figure 10:
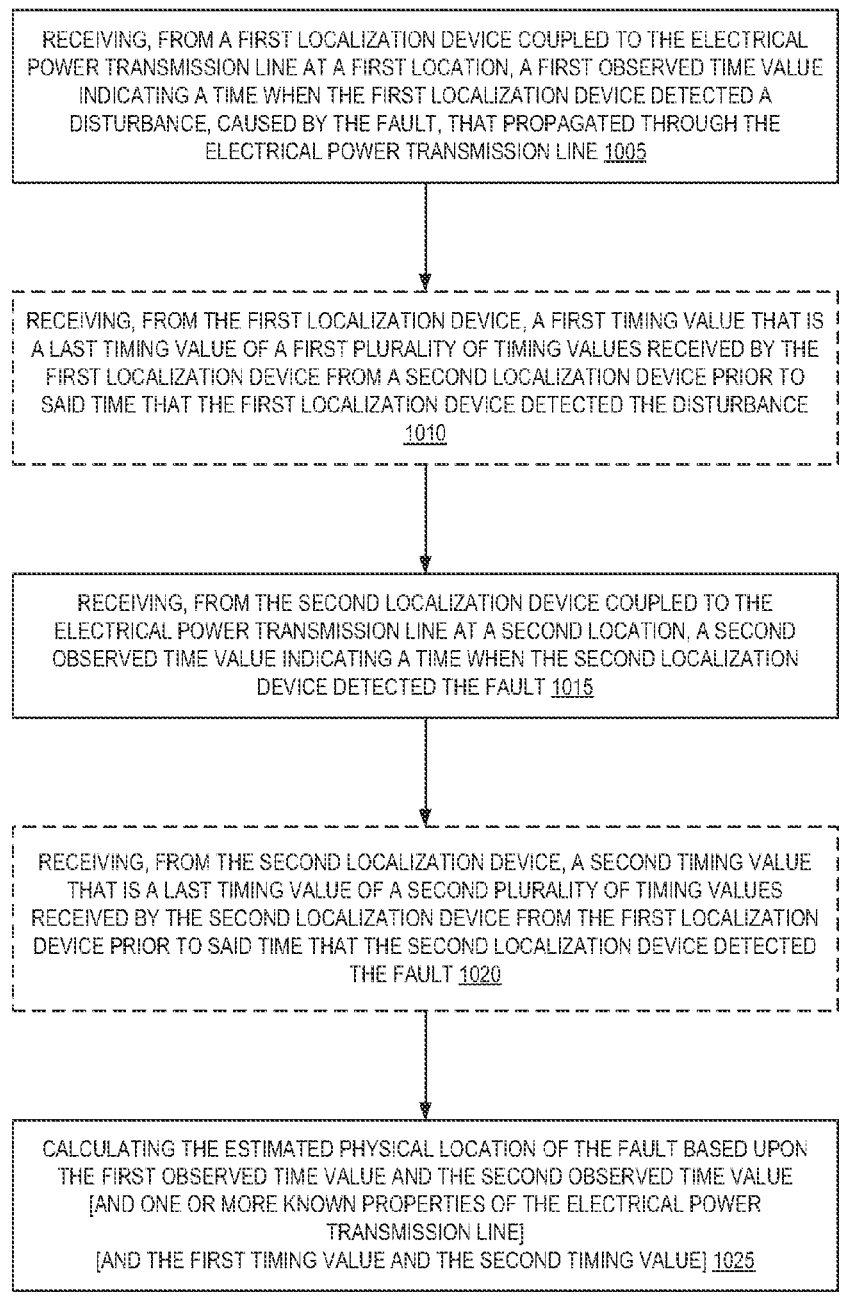
FIG. 10 illustrates a flow for determining an estimated physical location of a fault in an electrical power transmission line by a computing device according to an embodiment of the invention.

Electrical power transmission line fault localization may also be performed by a computing device separate from the localization devices that are coupled to the electrical power transmission line. FIG. 10 illustrates a flow 1000 for determining an estimated physical location of a fault in an electrical power transmission line by such a computing device according to an embodiment of the invention. At block 1005, the computing device receives, from a first localization device coupled to the electrical power transmission line at a first location, a first observed time value. The first observed time value indicates a time when the first localization device detected a disturbance, caused by the fault, which propagated through the electrical power transmission line. In an embodiment, the disturbance is a change in one or more of a current or voltage of the electrical power transmission line.

In those embodiments of the invention utilizing timing information transmitted over the electrical power transmission line to calculate the estimated physical location of the fault, the flow 1000 includes the computing device receiving, from the first localization device, a first timing value 1010. The first timing value is a last timing value of a first plurality of timing values received by the first localization device from a second localization device (coupled to the electrical power transmission line at a second location) prior to the time that the first localization device detected the disturbance.

The computing device also receives a second observed time value 1015 from the second localization device. The second observed time value indicates a time when the second localization device detected the fault. In an embodiment, the second localization device detects the fault by detecting the arrival of a disturbance at the second location. In an embodiment, the disturbance is one or more of a change in current and voltage of the electrical power transmission line.

In those embodiments of the invention utilizing timing information transmitted over the electrical power transmission line, the flow 1000 may also include the computing device receiving, from the second localization device, a second timing value 1020. The second timing value is a last timing value of a second plurality of timing values received by the second localization device from the first localization device prior to said time that the second localization device detected the fault.

Then, at block 1025, the computing device calculates the estimated physical location of the fault based upon the first observed time value and the second observed time value. In an embodiment of the invention, the calculation is also based upon one or more known properties of the electrical power transmission line. In an embodiment, the one or more known properties of the electrical power transmission line include one or more of a propagation velocity of electromagnetic waves transmitted using the electrical power transmission line and a length of the electrical power transmission line. In some embodiments, the calculation is optionally further based upon the first timing value and the second timing value.

In an embodiment, the estimated physical location of the fault is transmitted to a computing device to notify or otherwise present to a user the estimated physical location of the fault. In an embodiment, the estimated physical location of the fault is displayed to a user, through one or more of a projector, monitor, television, computing device display/screen, physical print-out, etc.

While the flow diagrams in the figures show a particular order of operations performed by certain embodiments of the invention, it should be understood that such order is exemplary (e.g., alternative embodiments may perform the operations in a different order, combine certain operations, overlap certain operations, etc.).

Additionally, while the invention has been described in terms of several embodiments, those skilled in the art will recognize that the invention is not limited to the embodiments described, can be practiced with modification and alteration within the spirit and scope of the appended claims. The description is thus to be regarded as illustrative instead of limiting.

The invention claimed is:
1. A method in a localization device coupled to a pipeline at a first location for determining an estimated physical location of a fault in the pipeline, the method comprising:

detecting, by the localization device, a disturbance caused by the fault, wherein the disturbance comprises one or more of,
an arrival of an acoustic wave at the first location, and
a change, at the first location, in a flow rate or pressure of matter transmitted through the pipeline;
determining a first observed time value indicating a time when the localization device performed said detecting of the disturbance;
receiving, from a second localization device coupled to the pipeline at a second location, a second observed time value indicating a time when the second localization device detected the fault; and
calculating the estimated physical location of the fault based upon the first observed time value and the second observed time value.

2. The method of claim 1, further comprising:
receiving, by the localization device, a first plurality of timing values transmitted by the second localization device;
transmitting, by the localization device, a second plurality of timing values to the second localization device;
determining, by the localization device, that a first timing value of the first plurality of timing values is a last timing value of the first plurality of timing values received by the localization device prior to said detecting of the disturbance; and
receiving, by the localization device, a second timing value from the second localization device that is a last timing value of the second plurality of timing values received by the second localization device prior to said time when the second localization device detected the fault,
wherein said calculating of the estimated physical location of the fault is further based upon the first timing value and the second timing value.

3. The method of claim 2, wherein the first plurality of timing values and the second plurality of timing values are transmitted through the pipeline.

4. The method of claim 3, wherein each timing value of the first plurality of timing values comprises a plurality of acoustically-encoded bits.

5. The method of claim 3, wherein each timing value of the first plurality of timing values comprises one or more acoustically-encoded unambiguous single tone or complex multi-tone sequences.

6. The method of claim 3, wherein each timing value of the first plurality of timing values is represented by an acoustically-encoded pseudo-random binary sequence (PRBS) selected such that a sliding window value of the PRBS is unambiguous.

7. The method of claim 1, wherein said calculating of the estimated physical location of the fault is further based upon one or more of:
a propagation velocity of matter transmitted through the pipeline;
a propagation velocity of acoustic waves transmitted through the matter in the pipeline or transmitted through the walls of the pipeline;
a length of the pipeline between the first location and the second location; and
an acoustic wave propagation delay of the pipeline between the first location and the second location.

8. A method in a computing device for determining an estimated physical location of a fault in a pipeline, the method comprising:
receiving, from a first localization device coupled to the pipeline at a first location, a first observed time value indicating a time when the first localization device detected a disturbance caused by the fault, wherein the disturbance comprises one or more of,
an arrival of an acoustic wave at the first location, and
a change, at the first location, in a flow rate or pressure of matter transmitted through the pipeline;
receiving, from a second localization device coupled to the pipeline at a second location, a second observed time value indicating a time when the second localization device detected the fault; and
calculating the estimated physical location of the fault based upon the first observed time value and the second observed time value.

9. The method of claim 8, further comprising:
receiving, from the first localization device, a first timing value that is a last timing value of a first plurality of timing values received by the first localization device from the second localization device prior to said time that the first localization device detected the disturbance; and
receiving, from the second localization device, a second timing value that is a last timing value of a second plurality of timing values received by the second localization device from the first localization device prior to said time that the second localization device detected the fault,
wherein said calculating of the estimated physical location of the fault is further based upon the first timing value and the second timing value.

10. The method of claim 9, wherein the first plurality of timing values and the second plurality of timing values are transmitted through the pipeline.

11. The method of claim 10, wherein each timing value of the first plurality of timing values comprises a plurality of acoustically-encoded bits.

12. The method of claim 10, wherein each timing value of the first plurality of timing values comprises one or more acoustically-encoded unambiguous single or complex tones or tone sequences.

13. The method of claim 10, wherein each timing value of the first plurality of timing values is represented by an acoustically-encoded pseudo-random binary sequence (PRBS) selected such that a sliding window value of the PRBS is unambiguous.

14. The method of claim 8, wherein said calculating of the estimated physical location of the fault is further based upon one or more of:
a propagation velocity of matter transmitted through the pipeline;
a propagation velocity of acoustic waves transmitted through the matter in the pipeline or transmitted through the walls of the pipeline;
a length of the pipeline between the first location and the second location; and
an acoustic wave propagation delay of the pipeline between the first location and the second location.

15. A method in a localization device coupled to an electrical power transmission line at a first location for determining an estimated physical location of a fault in the electrical power transmission line, the method comprising:
detecting, by the localization device, a disturbance caused by the fault, wherein the disturbance propagated through the electrical power transmission line;
determining a first observed time value indicating a time when the localization device performed said detecting of the disturbance;

receiving, from a second localization device coupled to the electrical power transmission line at a second location, a second observed time value indicating a time when the second localization device detected the fault; and calculating the estimated physical location of the fault based upon the first observed time value and the second observed time value.

16. The method of claim 15, further comprising:

receiving, by the localization device, a first plurality of timing values transmitted using the electrical power transmission line by the second localization device;

transmitting, by the localization device, a second plurality of timing values using the electrical power transmission line to the second localization device;

determining, by the localization device, that a first timing value of the first plurality of timing values is a last timing value of the first plurality of timing values received by the localization device prior to said detecting of the disturbance by the localization device; and receiving, by the localization device, a second timing value from the second localization device that is a last timing value of the second plurality of timing values received by the second localization device prior to said time when the second localization device detected the fault, wherein said calculating of the estimated physical location of the fault is further based upon the first timing value and the second timing value.

17. The method of claim 16, wherein one or both of the first plurality of timing values and the second plurality of timing values is represented by a Pseudo-Random Binary Sequence (PRBS).

18. The method of claim 17, wherein the PRBS is generated such that each timing value corresponds to a value of a sliding window of bits, wherein a size of the sliding window is selected to create unambiguous values.

19. The method of claim 16, wherein one or both of the first plurality of timing values and the second plurality of timing values are transmitted by impressing a modulated carrier signal on the electrical power transmission line.

20. The method of claim 16, wherein said calculating is further based upon one or more of:

a propagation velocity of electromagnetic energy transmitted using the electrical power transmission line; and a length of the electrical power transmission line between the first location and the second location.

21. A method in a computing device for determining an estimated physical location of a fault in an electrical power transmission line, the method comprising:

receiving, from a first localization device coupled to the electrical power transmission line at a first location, a first observed time value indicating a time when the first localization device detected a disturbance, caused by the fault, that propagated through the electrical power transmission line;

receiving, from a second localization device coupled to the electrical power transmission line at a second location, a second observed time value indicating a time when the second localization device detected the fault; and calculating the estimated physical location of the fault based upon the first observed time value and the second observed time value.

22. The method of claim 21, further comprising:

receiving, from the first localization device, a first timing value that is a last timing value of a first plurality of timing values received by the first localization device from the second localization device prior to said time that the first localization device detected the disturbance; and receiving, from the second localization device, a second timing value that is a last timing value of a second plurality of timing values received by the second localization device from the first localization device prior to said time that the second localization device detected the fault, wherein said calculating of the estimated physical location of the fault is further based upon the first timing value and the second timing value.

23. The method of claim 22, wherein one or both of the first plurality of timing values and the second plurality of timing values is represented by a Pseudo-Random Binary Sequence (PRBS).

24. The method of claim 21, wherein said calculating is further based upon one or more of:

a propagation velocity of electromagnetic energy transmitted using the electrical power transmission line; and a length of the electrical power transmission line between the first location and the second location.

* * * * *

UNITED STATES PATENT AND TRADEMARK OFFICE
CERTIFICATE OF CORRECTION

PATENT NO.         : 9,164,065 B2                                       Page 1 of 1
APPLICATION NO.    : 13/797589
DATED              : October 20, 2015
INVENTOR(S)        : Hood et al.

It is certified that error appears in the above-identified patent and that said Letters Patent is hereby corrected as shown below:

In Column 18, Line 12, delete "810B" and insert -- 'B' 810B --, therefor.

In Column 18, Line 16, delete "810B" and insert -- 'B' 810B --, therefor.

Signed and Sealed this
Twenty-second Day of March, 2016

Michelle K. Lee
*Director of the United States Patent and Trademark Office*